US00PP36634P2

(12) United States Plant Patent
Mousa

(10) Patent No.: US PP36,634 P2
(45) Date of Patent: Apr. 29, 2025

(54) ***DAHLIA* PLANT NAMED 'Dodasumbepubi'**

(50) Latin Name: *Dahlia variabilis*
Varietal Denomination: Dodasumbepubi

(71) Applicant: DUMMEN GROUP B.V., De Lier (NL)

(72) Inventor: Rami Mousa, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/665,078

(22) Filed: May 15, 2024

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC . A01H 5/02; A01H 5/00; A01H 6/144; A01H 6/14
See application file for complete search history.

(56) References Cited

PUBLICATIONS

Gabot.de 2023 Dummen Orange: Many new products in the show garden, retrieved on Aug. 20, 2024 at https://www.gabot.de/ansicht/duemmen-orange-viele-neuheiten-im-schaugarten-423399.html, 7 pp. (Year: 2023).*
YouTube video Flower Trials 2023—*Dahlia* Summer Beens ENG, retrieved on Aug. 20, 2024 at https://www.youtube.com/watch?v=4J2vDUm8Qgo, one page. (Year: 2023).*

* cited by examiner

*Primary Examiner* — June Hwu
(74) *Attorney, Agent, or Firm* — C. Anne Whealy

(57) ABSTRACT

A new and distinct cultivar of *Dahlia* plant named 'Dodasumbepubi', characterized by its upright and uniformly mounding plant habit; moderately vigorous growth habit and moderate growth rate; freely branching habit; dark green-colored leaves; freely flowering habit; large single-type inflorescences with reddish purple and light yellow bi-colored ray florets; good postproduction longevity; good garden performance; and attractiveness to pollinators.

1 Drawing Sheet

Botanical designation: *Dahlia variabilis*.
Cultivar denomination: 'DODASUMBEPUBI'.

CROSS-REFERENCED TO CLOSELY-RELATED APPLICATIONS

Title: *Dahlia* Plant Named 'Dodasumberebic'
Inventor: Rami Mousa
Filed: May 15, 2024; U.S. Plant patent application Ser. No. 18/665,111

STATEMENT REGARDING PRIOR DISCLOSURES BY INVENTOR AND APPLICANT/ASSIGNEE

An European Community Plant Breeder's Rights application for the instant plant was filed by the Applicant/Assignee, Dümmen Group B.V. of De Lier, The Netherlands on Nov. 15, 2023, application number 2023/2278. Foreign priority is not claimed to this application.

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Dahlia* plant, botanically known as *Dahlia variabilis* and hereinafter referred to by the name 'Dodasumbepubi'.

The new *Dahlia* plant is a product of a planned breeding program conducted by the Inventor in De Lier, The Netherlands. The objective of the breeding program is to create new container *Dahlia* plants that have a freely branching and flowering habit, strong leaves, large attractive inflorescences and good postproduction longevity and garden performance.

The new *Dahlia* plant originated from a cross-pollination during the autumn of 2018 in De Lier, The Netherlands of a proprietary selection of *Dahlia variabilis* identified as code number DA-0736, not patented, as the female, or seed, parent with a proprietary selection of *Dahlia variabilis* identified as code number DA-2014, not patented, as the male, or pollen, patent. The new *Dahlia* plant was discovered and selected by the Inventors as a single flowering plant from within the progeny of the stated cross-pollination in a controlled greenhouse environment in De Lier, The Netherlands during the summer of 2019.

Asexual reproduction of the new *Dahlia* plant by vegetative terminal cuttings in a controlled greenhouse environment in De Lier, The Netherlands since the autumn of 2019 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dodasumbepubi'. These characteristics in combination distinguish 'Dodasumbepubi' as a new and distinct *Dahlia* plant:

1. Upright and uniformly mounding plant habit.
2. Moderately vigorous growth habit and moderate growth rate.
3. Freely branching habit.
4. Dark green-colored leaves.
5. Freely flowering habit.
6. Large single-type inflorescences with reddish purple and light yellow bi-colored ray florets.
7. Good postproduction longevity.
8. Good garden performance and attractive to pollinators.

Compared to plants of the female parent selection, plants of the new *Dahlia* differ primarily in ray floret color as plants of the new *Dahlia* have reddish purple and light yellow bi-colored ray florets whereas plants of the female parent selection have solid white-colored ray florets. In addition, plants of the new *Dahlia* have single-type inflorescences whereas plants of the female parent selection have double-type inflorescences.

Compared to plants of the male parent selection, plants of the new *Dahlia* differ primarily in ray floret color as plants of the new *Dahlia* have reddish purple and light yellow bi-colored ray florets whereas plants of the male parent selection have solid light yellow-colored ray florets. In addition, plants of the new *Dahlia* have stronger garden performance than plants of the male parent selection.

Plants of the new *Dahlia* can be compared to plants of *Dahlia variabilis* 'Dodasumberebic', disclosed in a U.S. Plant Patent application filed concurrently. In side-by-side comparisons, plants of the new *Dahlia* differ primarily from plants of 'Dodasumberebic' in the following characteristics:

1. Plants of the new *Dahlia* are larger than plants of 'Dodasumberebic'.
2. Plants of the new *Dahlia* have smaller leaves than plants of 'Dodasumberebic'.
3. Ray florets of plants of the new *Dahlia* are reddish purple and light yellow bi-colored whereas ray florets of plants of 'Dodasumberebic' are bright red and yellow bi-colored.

BRIEF DESCRIPTION OF THE PHOTOGRAPH

The accompanying photograph illustrates the overall appearance of the new *Dahlia* plant showing the colors as true as it is reasonably possible to obtain in colored reproductions of this type. Colors in the photograph may differ slightly from the color values cited in the detailed botanical description which accurately describe the colors of the new *Dahlia* plant. The photograph is a side perspective view of a typical flowering plant of 'Dodasumbepubi' grown in a container.

DETAILED BOTANICAL DESCRIPTION

The aforementioned photograph and the following observations and measurements describe plants grown during the summer in 15-cm containers in a glass-covered greenhouse in De Lier, The Netherlands and under environmental conditions and cultural practices which approximate those generally used in commercial potted *Dahlia* production. During the production of the plants, day temperatures ranged from 18° C. to 30° C., night temperatures ranged from 16° C. to 22° C. and light levels were at least 135 watt/m$^2$. Plants were pinched one time about four weeks after sticking unrooted cuttings. Plants were twelve weeks old when the photograph was taken and eleven weeks old when the description was taken. In the following description, color references are made to The Royal Horticultural Society Colour Chart, Fifth Edition, except where general terms of ordinary dictionary significance are used.

Botanical classification: *Dahlia variabilis* 'Dodasumbepubi'.

Parentage:

*Female, or seed, parent.*—Proprietary selection of *Dahlia variabilis* identified as code number DA-0736, not patented.

*Male, or pollen, parent.*—Proprietary selection of *Dahlia variabilis* identified as code number DA-2014, not patented.

Propagation:

*Type.*—By vegetative terminal cuttings.

*Time to initiate roots, summer.*—About 12 days at temperatures about 22° C. to 30° C.

*Time to initiate roots, winter.*—About 14 days at temperatures about 20° C. to 22° C.

*Time to produce a rooted plant, summer.*—About 21 days at temperatures about 22° C. to 30° C.

*Time to produce a rooted plant, winter.*—About 24 days at temperatures about 20° C. to 22° C.

*Root description.*—Medium in thickness, fibrous; typically whitish grey in color, actual color of the roots is dependent on substrate composition, water quality, fertilizers, substrate temperature and age of roots; tuber development has not been observed on plants of the new *Dahlia*.

*Rooting habit.*—Moderately freely branching; medium density.

Plant description:

*Plant and growth habit.*—Upright and uniformly mounding plant form; overall shape, globose; freely basal branching habit with about four to six primary lateral branches per plant, each primary lateral branch with about five to seven secondary lateral branches; pinching is not required, however, pinching will enhance lateral branch development; inflorescences held above the foliar plane on moderately strong peduncles; bushy and dense habit; moderately vigorous growth habit and moderate growth rate.

*Plant height, soil level to top of foliar plane.*—About 25 cm.

*Plant height, soil level to top of floral plane.*—About 36 cm.

*Plant diameter or spread.*—About 33 cm.

*Lateral branches.*—Length: About 23 cm. Diameter: About 6 mm to 8 mm. Internode length: About 2 cm to 6 cm. Aspect: Mostly upright. Strength: Moderately strong. Texture and luster: Smooth, glabrous; semi-glossy. Color, developing and developed: Close to 143C.

Leaf description:

*Arrangement.*—Opposite, single; to date, compound leaf development has not been observed on plants of the new *Dahlia*.

*Length.*—About 10 cm.

*Width*.—About 6.5 cm.

*Shape*.—Ovate.

*Apex*.—Acute.

*Base*.—Attenuate.

*Margin*.—Dentate; leaves occasionally lobed with shallow and divergent indentations.

*Venation pattern*.—Pinnate.

*Texture and luster, upper surface*.—Smooth, glabrous; semi-glossy.

*Leaf and leaflet texture and luster, lower surface*.—Smooth, glabrous; matte.

*Color*.—Developing leaves, upper surface: Close to 137B. Developing leaves, lower surface: Close to 138B. Fully expanded leaves, upper surface: Close to 137A; venation, close to 138B. Fully expanded leaves, lower surface: Close to 138B; venation, close to 143B.

*Petioles*.—Length: About 6.5 cm. Diameter: About 4 mm. Strength: Moderately strong. Texture and luster, upper and lower surfaces: Smooth, glabrous; semi-glossy. Color, upper and lower surfaces: Close to 144A.

Inflorescence description:

*Appearance and arrangement*.—Single-type inflorescence form with ray florets forming acropetally on a receptacle; inflorescences positioned above the foliar plane on moderately strong peduncles; inflorescences face mostly upright; freely flowering habit with about 23 developing and fully developed inflorescences per plant at one time.

*Fragrance*.—None detected.

*Time to flower*.—Early flowering habit, plants begin flowering about ten weeks after planting; in the garden in The Netherlands, plants flower continuously from spring until late summer.

*Post-production longevity*.—Inflorescences maintain good substance for about two to three weeks on the plant; inflorescences persistent.

*Inflorescence buds*.—Height: About 9 mm. Diameter: About 9 mm. Shape: Globular. Texture and luster: Smooth, glabrous; glossy. Color: Close to 144B.

*Inflorescence size*.—Diameter: Large, about 10 cm. Depth (height): About 1.5 cm to 2 cm. Disc diameter: About 1.5 cm to 1.8 cm. Receptacle height: About 2 mm to 3 mm. Receptacle diameter: About 1.5 cm. Receptacle color: Close to 144A.

*Ray florets*.—Quantity per inflorescence: About ten in a single whorl. Length: About 4.5 cm. Width: About 2.5 cm. Shape: Oblong to ligulate. Apex: Retuse. Base: Attenuate. Margin: Entire; not undulate. Aspect: Initially upright to outwardly with development. Texture and luster, upper and lower surfaces: Smooth, glabrous; matte. Color: When opening and fully opened, upper surface: Close to 78A; towards the base, close to 3C and 4D; venation, similar to lamina colors or close to 12D; colors do not change with subsequent development. When opening and fully opened, lower surface: Close to 80B; towards the base, close to 4D; venation, similar to lamina colors or close to 12D; colors do not change with subsequent development.

*Disc florets*.—Quantity per inflorescence: About 50 to 60. Length: About 1.3 cm. Diameter: About 1 mm. Shape: Tubular, elongated; apices retuse. Texture and luster: Smooth, glabrous; glossy. Color, when opening, inner and outer surfaces: Close to 12B. Color, fully opened, inner and outer surfaces: Close to 17B.

*Phyllaries*.—Quantity per inflorescence: About six arranged in a single whorl. Length: About 1.8 cm. Width: About 5 mm to 8 mm. Shape: Ovate. Apex: Acute. Base: Attenuate. Margin: Entire. Texture and luster, upper and lower surfaces: Smooth, glabrous; semi-glossy. Color, upper surface: Close to 137A. Color, lower surface: Close to 137B.

*Peduncles*.—Length, terminal peduncle: About 7 cm to 10 cm. Diameter, terminal peduncle: About 3 mm. Aspect: Mostly erect to slightly outwardly. Strength: Moderately strong. Texture and luster: Smooth, glabrous; semi-glossy. Color: Close to 144A.

*Reproductive organs*.—Androecium: Present on disc florets only. Stamen quantity per floret: Five to six. Filament length: About 1.3 cm. Filament color: Close to 12B. Anther length: About 7 mm. Anther color: Close to 17A and 25A. Pollen amount: Moderate. Pollen color: Close to 25A. Gynoecium: Present on disc florets only. Pistil quantity per floret: One. Pistil length: About 1 cm. Style length: About 5 mm. Style color: Close to 144D. Stigma diameter: Less than 1 mm. Stigma shape: Bifurcate. Stigma color: Close to 17B. Ovary color: Close to 145C. Seeds: To date, seed development has not been observed on plants of the new *Dahlia*.

Pathogen & pest resistance: To date, plants of the new *Dahlia* have not been observed to be resistant to pathogens and pests common to *Dahlia* plants.

Temperature tolerance & garden performance: Plants of the new *Dahlia* tolerate high temperatures about 35° C. and low temperatures about 10° C. Plants of the new *Dahlia* have been observed to have good garden performance and to be attractive to pollinators.

It is claimed:

1. A new and distinct *Dahlia* plant named 'Dodasumbepubi' as herein illustrated and described.

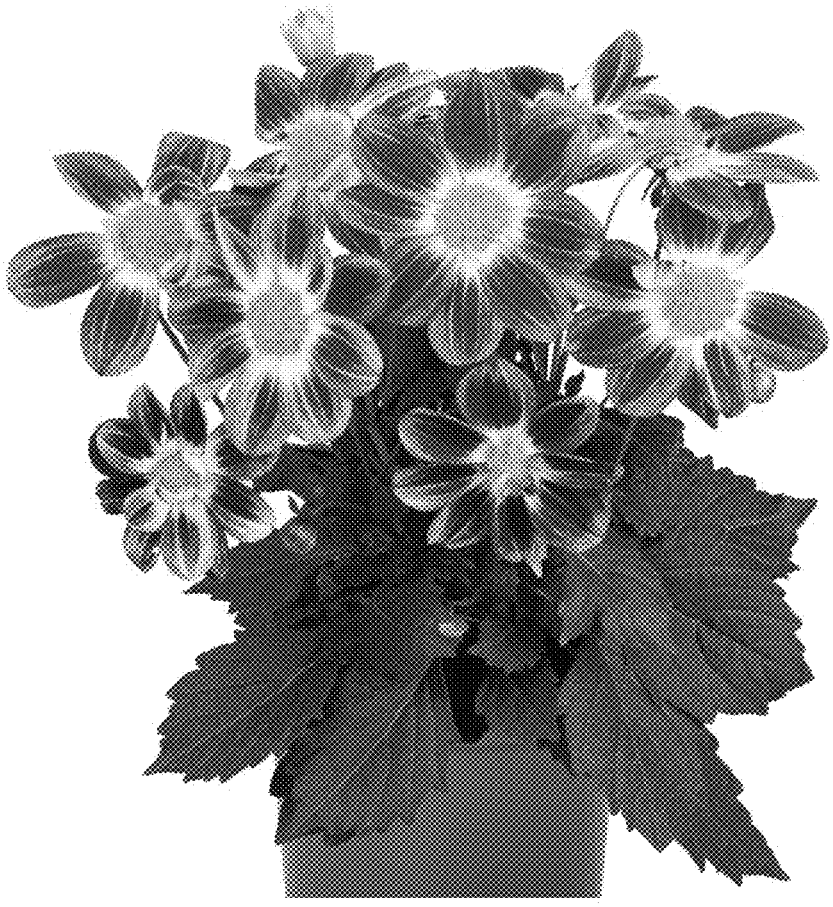

* * * * *